United States Patent
Kojo et al.

(10) Patent No.: US 11,806,106 B2
(45) Date of Patent: Nov. 7, 2023

(54) MAGNETICALLY GUIDED SURGICAL PROBE

(71) Applicant: GYRUS ACMI, INC., Westborough, MA (US)

(72) Inventors: Hiroyuki Kojo, Brookline, MA (US); Tara Hendrzak, Merrimack, NH (US)

(73) Assignee: Gyrus ACMI, Inc., Westborough, MA (US)

(*) Notice: Subject to any disclaimer, the term of this patent is extended or adjusted under 35 U.S.C. 154(b) by 280 days.

(21) Appl. No.: 17/108,254

(22) Filed: Dec. 1, 2020

(65) Prior Publication Data

US 2021/0169599 A1 Jun. 10, 2021

Related U.S. Application Data

(60) Provisional application No. 62/943,341, filed on Dec. 4, 2019.

(51) Int. Cl.
*A61B 34/00* (2016.01)
*A61B 17/34* (2006.01)
(Continued)

(52) U.S. Cl.
CPC .......... *A61B 34/73* (2016.02); *A61B 17/3478* (2013.01); *A61B 1/018* (2013.01);
(Continued)

(58) Field of Classification Search
CPC . A61B 34/73; A61B 17/3478; A61B 17/3403; A61B 17/34; A61B 1/018;
(Continued)

(56) References Cited

U.S. PATENT DOCUMENTS

| 2006/0144407 A1* | 7/2006 | Aliberto | A61M 25/0127 |
| | | | 600/431 |
| 2010/0113872 A1* | 5/2010 | Asada | A61B 17/3478 |
| | | | 600/102 |

(Continued)

FOREIGN PATENT DOCUMENTS

| CN | 114980825 A | 8/2022 | |
| WO | WO-2017075544 A1 * | 5/2017 | ........... A61M 25/04 |
| WO | WO-2021113214 A1 | 6/2021 | |

OTHER PUBLICATIONS

"International Application Serial No. PCT/US2020/062661, International Preliminary Report on Patentability dated Jun. 16, 2022", 8 pgs.

(Continued)

*Primary Examiner* — Shaun L David
*Assistant Examiner* — Rachael L Geiger
(74) *Attorney, Agent, or Firm* — Schwegman Lundberg & Woessner, P.A.

(57) ABSTRACT

A probe for use in an anatomical region of a patient. The probe can optionally include: a proximal portion; an insertion portion and a magnetizable element. The insertion portion can be coupled to the proximal portion and can extend distally thereof. The insertion portion can have an elongated extent and a longitudinal axis. The insertion portion can include a flexible section. The magnetizable element can be positioned at a distal end portion of the insertion portion and can be configured for use within the anatomical region to produce a magnetic force between the magnetizable element and an extracorporeal magnetizable element that can direct the distal end portion of the probe to a desired location within the anatomic region.

10 Claims, 8 Drawing Sheets

(51) Int. Cl.
*A61B 1/018* (2006.01)
*A61B 17/00* (2006.01)

(52) U.S. Cl.
CPC ............... *A61B 2017/00278* (2013.01); *A61B 2034/731* (2016.02)

(58) Field of Classification Search
CPC ........... A61B 2017/00278; A61B 2017/00876; A61B 2034/731; A61B 2034/733
See application file for complete search history.

(56) References Cited

U.S. PATENT DOCUMENTS

| | | |
|---|---|---|
| 2013/0317338 A1 | 11/2013 | Silverstein |
| 2015/0165187 A1 | 6/2015 | Liu |
| 2020/0289152 A1* | 9/2020 | Swensen ............ A61B 17/3478 |

OTHER PUBLICATIONS

"International Application Serial No. PCT US2020 062661, International Search Report dated Feb. 18, 2021", 6 pgs.
"International Application Serial No. PCT US2020 062661, Written Opinion dated Feb. 18, 2021", 6 pgs.

* cited by examiner

MAGNETICALLY GUIDED SURGICAL PROBE

CROSS-REFERENCE TO RELATED APPLICATION

This application claims the benefit of priority to U.S. Provisional Patent Application Ser. No. 62/943,341, filed on Dec. 4, 2019, the contents of which are incorporated herein in their entirety.

TECHNICAL FIELD

This document pertains generally, but not by way of limitation, to surgical devices, and more particularly, to a surgical probe that is magnetically guidable.

BACKGROUND

Various surgical techniques have been developed for treating kidney stones. Treatment can be performed endoscopically or laparoscopically, for example. Thus, depending on various factors including the size of the stone, the manner of treatment can be selected. If the kidney stone is greater than about 20 mm in diameter, the kidney stone will generally need to be positionally identified and then a planned percutaneous nephrostomy procedure can be performed. This procedure prepares for a percutaneous nephrolithotomy (PCNL) procedure where a percutaneous nephrolithotomy needle is extracorporeally positioned external of the patient. The needle is then inserted from the external location through the patient's back to the target location such as a calyx of the kidney. Various stone fragmentation devices and stone retrieval devices can then be utilized with the access pathway created by the needle.

PCNL relies on precise positioning to locate the targeted calyx (the particular surgical target) without disturbing nearby structures of the kidney that may adversely affect the surgical results. As such, it requires substantial skill. Failure to adequately locate and access the targeted calyx can result in multiple access attempts, injury to the kidney or adjacent organs, increased procedure time, increased cost spent on the procedure and post-treatment recovery and increased patient blood loss and the probability of complications.

Due to the above challenges, alternative techniques such a retrograde puncture from the kidney outward using a retrograde nephrostomy needle have been developed. However, generating sufficient force for performing the puncture effectively has been difficult. Thus, this retrograde puncture technique has not gained wide adoption.

Overview

The following examples and discussion illustrate various configurations of the disclosed approach. In one example configuration, the proposed approach uses an in vivo surgical probe having a magnetizable element and extracorporeal magnetizable actuator that facilitates, aids or helps manipulation (e.g., directing) of a distal end portion of the surgical probe to a desired location such as to be positioned relative to an anatomical feature such as a targeted calyx of the kidney. The present inventors have also recognized that the magnetizable element and extracorporeal magnetizable actuator can additionally or alternatively be used to perform a retrograde puncture according to further examples. Thus, the present inventors have recognized, among other things, techniques, apparatuses, systems and methods that vitiate the challenges of the PCNL discussed above such as adequately positionally identifying the targeted calyx and determining a proper extracorporeal position for the needle so that the needle is properly aligned with the targeted calyx. Furthermore, the present inventors have recognized techniques, apparatuses, systems and methods that address the challenges such as lack of adequate force for performing the retrograde puncture as discussed above. The techniques, apparatuses, systems and methods of the present application can provide for a quicker and more accurate manipulation within (and from) the kidney and access to the targeted calyx without damaging ancillary portions of the kidney. This, in turn, reduces the risk associated with radiation visualization, the time and cost spent on the procedure, patient blood loss due to multiple/faulty attempted access and the probability of complications due to multiple/faulty attempted access.

The term "magnetizable" as used herein includes materials that exhibit ferrimagnetism (materials that have permanent magnetism) and materials that exhibit ferromagnetism (materials that can be magnetized). The term "magnetizable" means capable of being magnetized or already in a magnetized state. The term "magnetizable" also means that the item being referred to is magnetic or can be made magnetic using an applied electrical current or magnetic field.

Example 1 is a probe for use in an anatomical region of a patient. The probe can optionally include: a proximal portion; an insertion portion and a magnetizable element. The insertion portion can be coupled to the proximal portion and can extend distally thereof. The insertion portion can have an elongated extent and a longitudinal axis. The insertion portion can include a flexible section. The magnetizable element can be positioned at a distal end portion of the insertion portion and can be configured for use within the anatomical region to produce a magnetic force between the magnetizable element and an extracorporeal magnetizable element that can direct the distal end portion of the probe to a desired location within the anatomic region.

Example 2 is the probe of Example 1, wherein the magnet force that can direct the distal end portion of the probe is between 0.2 N and 0.4 N.

Example 3 is the probe of Example 1, further optionally comprising a needle that can be extendable from the distal end portion of the probe. The magnetizable element can be coupled to or can form at least a part of the needle. The needle can be configured to perform a retrograde puncture in response to the magnetic force attracting the magnetizable element toward the extracorporeal magnetizable actuator to form an access channel that can extend generally between the target anatomical region and a dermis adjacent to the extracorporeal magnetizable actuator.

Example 4 is the probe of Example 3, wherein the magnet force that can perform the retrograde puncture is between 0.9 N and 1.5 N.

Example 5 is the probe of Example 3, wherein the needle can be a part of a separate device from the probe and can pass through a working pathway of the probe to the distal end portion of the probe.

Example 6 is the probe of any one or any combination of Examples 1-5, wherein the magnetizable element can comprise a tube or sleeve that can be configured to be inserted in or coupled around the insertion portion or needle.

Example 7 is the probe of any one or any combination of Examples 1-6, wherein the magnetizable element can be arranged transverse to a longitudinal axis of the insertion portion at the distal end portion such that a first pole of the magnetizable element can be located more closely adjacent to a distal tip of the probe than a second pole of the magnetizable element.

Example 8 is the probe of any one or any combination of Examples 1-7, wherein the magnetizable element can be configured to bend the distal end portion of the probe to the desired location.

Example 9 is a puncturing probe for performing a retrograde from a target anatomical region of a patient. The probe can optionally comprise: an insertion portion configured to access the target anatomical region and a needle. The needle can be a needle coupled to a distal end of the insertion portion, wherein the needle has a magnetizable element that is coupled thereto or that forms at least a part of the needle, and wherein the needle is configured to perform the retrograde puncture in response to a magnetic field of an extracorporeal magnetizable actuator to form an access channel that extends generally between the target anatomical region and a dermis adjacent to the extracorporeal magnetizable actuator.

Example 10 is the puncturing probe of Example 9, wherein the magnet force can be between 0.9 N and 1.5 N.

Example 11, is the puncturing probe of any or any combination of Examples 9-10, wherein the magnetizable element can comprise a tube or sleeve configured to be inserted in or coupled around the insertion portion or needle.

Example 12 is a system for use in a target anatomical region of a patient. The system can optionally comprise a probe and an extracorporeal magnetizable actuator. The probe can optionally comprise: a proximal portion, an insertion portion and a magnetizable element. The insertion portion can be coupled to the proximal portion and can extend distal thereof. The insertion portion can have an elongated extent and a longitudinal axis. The insertion portion can includes a flexible section. The magnetizable element can be positioned at a distal end portion of the insertion portion and can be configured for use within the anatomical region. The extracorporeal magnetizable actuator can be configured to attract the magnetizable element with a magnetic force that can direct the distal end portion of the probe to the target anatomical region.

Example 13 is the system of Example 12, wherein the magnetic force that can direct the distal end portion of the probe is between 0.2 N and 0.4 N.

Example 14 is the system of Example 12, further optionally comprising a needle that can be at the distal end portion of the probe. The magnetizable element can be coupled to or can form at least a part of the needle. The needle can be configured to perform a retrograde puncture in response to the magnetic force attracting the magnetizable element toward an extracorporeal magnetizable actuator to form an access channel that can extend generally between the target anatomical region and a dermis adjacent to the extracorporeal magnetizable actuator.

Example 15 is the system of Example 13, wherein the magnet force to perform the retrograde puncture can be between 0.9 N and 1.5 N.

Example 16 is the system of Example 13, wherein the needle can be a part of a separate device from the probe and can pass through a working pathway of the probe to the distal end portion of the probe.

Example 17 is the system of any one or any combination of Examples 12-16, wherein the first magnet can be configured to be arranged transverse to a longitudinal axis of the insertion portion at the distal end portion such that a first pole of the first magnet can be located more closely adjacent to a distal tip of the probe than a second pole of the first magnet. The extracorporeal magnetizable actuator can have a first pole configured to interface with and can be more closely adjacent an epidermis than a second pole of the second magnet.

Example 18 is the system of any one or combination of Examples 12-17, wherein one of the extracorporeal magnetizable actuator or the magnetizable actuator can be a user-actuatable electromagnet.

Example 19 is a method for directing a probe to a target anatomical region. The method can optionally comprise: providing or obtaining the probe having a magnetizable element positioned at a distal end portion of the probe; and directing the distal end portion of the probe from an extracorporeal location with a magnetic force acting on the magnetizable element to position the distal end portion of the probe within the target anatomical region.

Example 20 is the method of Example 19, optionally further comprising performing a retrograde puncture in response to the magnetic field to form an access channel that can extend generally between the target anatomical region and a dermal portion.

Example 21 is the method of Example 20, wherein performing the retrograde puncture can comprise actuating a user-actuatable extracorporeal magnetizable actuator.

Example 22 is the method of any of Examples 19-20, optionally further comprising a extracorporeal magnetizable actuator that can be a permanent magnet. The extracorporeal magnetizable actuator can be placed against or adjacent the dermal region only after the distal end portion of the probe has been passed to the anatomic region.

Example 23 is the method of any of Examples 19-22, optionally further comprising performing one or both of endoscopic imaging and X-ray imaging contemporaneous with or prior to the positionally manipulating the distal end portion of the probe to the target location or performing the retrograde puncture.

Example 24 is any one or combination of the Examples or elements of the Examples 1-23.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present disclosure is directed to a surgical device comprising a probe and related systems and methods. Although described in reference to the treatment of kidney stones, it should be recognized that the apparatuses, systems, methods and techniques of the present application are not limited to this type of procedure. Indeed, the present apparatuses, systems, methods and techniques can be utilized in any procedure that relies on precise positioning of a probe and/or utilizes a retrograde puncture.

In this disclosure, relative terms, such as, for example, "about", "generally", or "substantially" are used to indicate a possible variation of ±10% in a stated numeric value or within ±10° of the numeric value.

Figure 1:
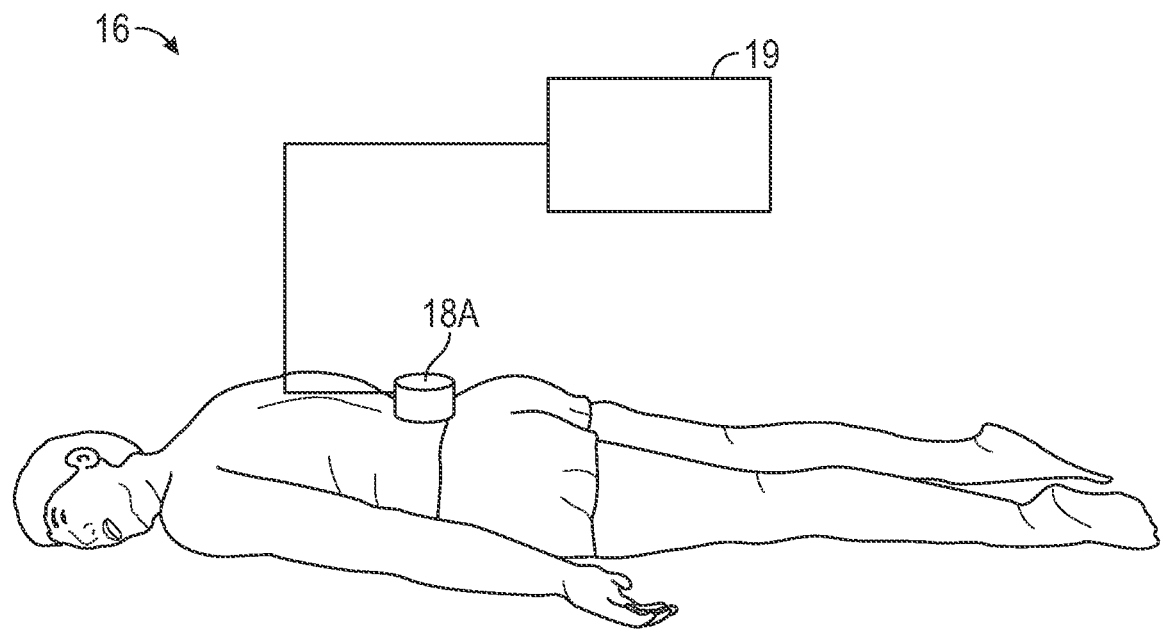
FIG. 1 is a schematic view of a patient in a supine position with an extracorporeal magnetizable actuator positioned at the back of the patient adjacent or abutting the dermis according to an example of the present application.

FIG. 1 shows extracorporeal portions of a system 16 for treating kidney stones of a patient P. In particular, the system 16 can include an extracorporeal magnetizable actuator 18A that can be used to positionally manipulate (e.g., direct such as by bending) a distal end portion of a probe (shown in FIG. 1A) within a kidney of the patient P. More particularly, a magnetic field and corresponding magnetic force between the extracorporeal magnetizable actuator 18A and another magnet coupled to or making up a distal end portion of the probe. According to some examples, the extracorporeal magnetizable actuator 18A and probe can be configured to perform a retrograde puncture from the kidney to or adjacent the extracorporeal magnetizable actuator 18A.

The extracorporeal magnetizable actuator 18A can be located at or adjacent a dermis D of the patient P such as on or adjacent a back of the patient. The extracorporeal magnetizable actuator 18A will be described in further detail subsequently in regard to FIG. 1A. According to one example, the extracorporeal magnetizable actuator 18A can be an electromagnet that can be selectively actuated by an actuation unit 19 that is electronically coupled with the extracorporeal magnetizable actuator 18A to provide current thereto.

Figure 1A:
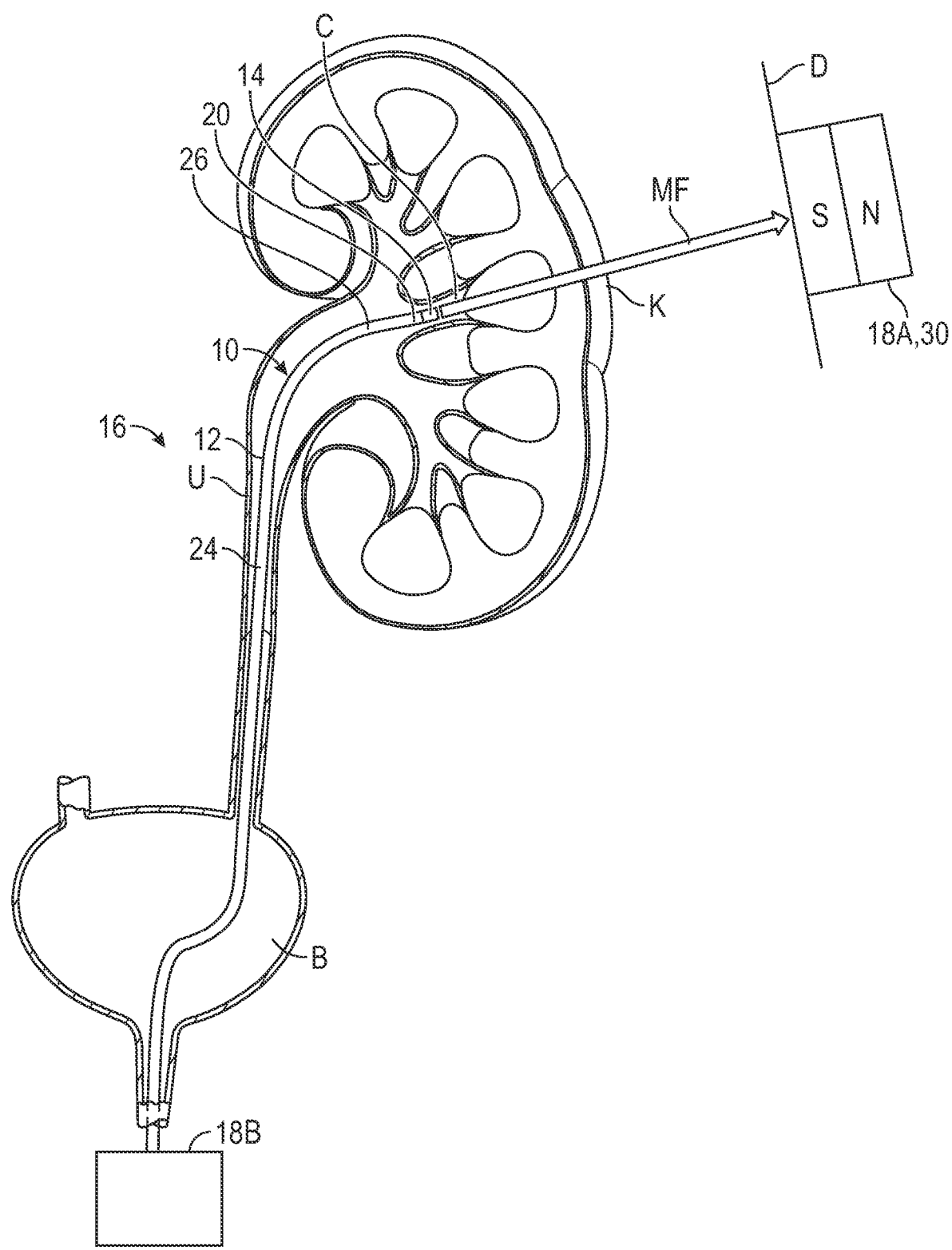
FIG. 1A is a schematic view of the system including a probe and the extracorporeal magnetizable actuator having a magnetic field between them acting to manipulate a distal end portion of the probe to be positioned in a desired location within an anatomical region of a patient according to an example the present application.

FIG. 1A is a schematic diagram of a probe 10 being positionally manipulated within a kidney K of the patient P by a magnetic field and corresponding magnetic force MF according to an example of the present application. The probe 10 can include an insertion portion 12 and a magnetizable element 14. The probe 10 can include other portions such as a proximal portion and/or actuator(s) not specifically illustrated. The probe 10 can be used as part of the system 16 that includes the extracorporeal magnetizable actuator 18A and/or an extracorporeal magnetizable actuator 18B.

As illustrated in FIG. 1A, the probe 10 can be configured to access the kidney K via a bladder B and a ureter U and can have a distal end portion 20 that can be positionally manipulatable within the kidney K to an in vivo target location that can comprise an anatomy such as a calyx C. Such manipulation can be performed with the aid of the magnetic force MF comprising an attraction between the magnetizable element and the extracorporeal magnetizable actuator 18A as discussed further herein.

In such location, the probe 10 can be configured to perform one or more functions such as to emit a signal used to identify the in situ target location or act with one or more other devices to perform other tasks such as to visualize the anatomy of the patient or treat a kidney stone, for example. As further illustrated in FIGS. 4-6, the probe 10 in some examples can be additionally or alternatively configured to perform a retrograde puncture. Thus, the probe 10 can include a needle 15 (FIGS. 4-6) or can provide an access pathway for the needle 15 to perform the retrograde puncture. Thus, the needle 15 can be a separate component configured for use with the probe according to some examples. As discussed previously, the probe 10 and/or needle 15 can be configured for precise puncturing to treat a variety of conditions and not just for the treatment of renal calculi. The retrograde puncture can be performed with the aid of the magnetic force MF and can create an access pathway from the target location within the kidney K as illustrated in FIG. 1A to an extracorporeal location on, at or adjacent a dermis D approximated by the extracorporeal magnetizable actuator 18A. The needle 15 can optionally include a lumen, and/or be otherwise configured to create the access pathway to be of a suitable size and shape for percutaneous access by a lithotripter, or other types of rigid or flexible instruments for surgical procedures to treat renal calculi or other ailments of the kidney K.

Figure 2:
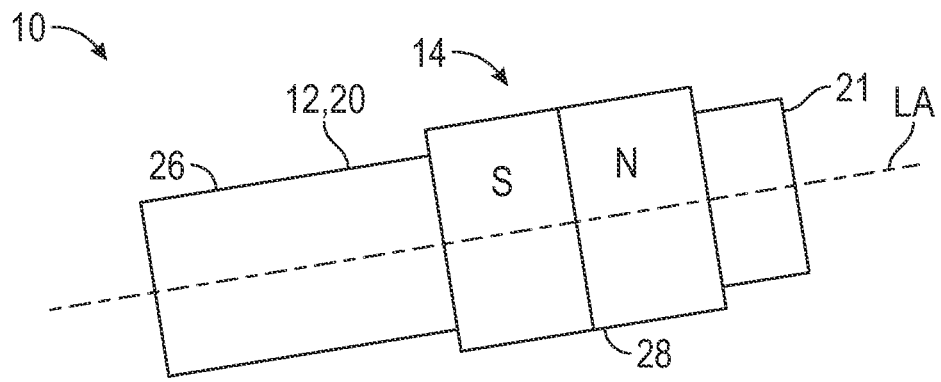
FIG. 2 is an enlarged schematic view of the distal end portion of the probe of FIG. 1 according to an example of the present application.

A description of the components of the probe 10 now follows. These components are optional and need not be included in various examples of the probe 10. Other components are contemplated for use with the probe 10 but are not specifically illustrated in the example of FIG. 1A. The insertion portion 12 can include the distal end portion 20. The insertion portion 12 can be configured as a tube or shaft having an elongated extent and a longitudinal axis LA (FIG. 2). The insertion portion 12 can provide a working channel or pathway for other components such as the needle 15 (FIGS. 4-6) to be manipulated at the distal end portion 20 of the probe 10.

To access the kidney K via the ureter U, the insertion portion 12 can be appropriately sized and can have a flexible section 24. The insertion portion 12 can also have a bending section 26 distal of the flexible section 24. The bending section 26 can be configured to be manipulatable (such as by magnetic force MF, motor and/or another type of actuator) to bend, twist or otherwise be manipulated within and adjacent the kidney K such as illustrated in FIG. 1A to position the distal tip of the probe 10 within, aligned with, abutting or adjacent one of the calyx C, for example. This calyx C can be the target location for treatment as previously described and can be selected based upon the location of the kidney stone(s), ease of pathway for a retrograde puncture or other reasons. Positioning of the probe 10 within the kidney K and at the target location (e.g., aligned with, abutting or adjacent one or more of the calyx C) can be facilitated by endoscopic imaging and/or with the support of X-ray or another type of imaging (CT, ultrasound, MRI, etc.) in addition to the magnetic force MF, motor and/or other actuator, for example.

As shown in FIG. 2, the magnetizable element 14 can be coupled to or be an integral part of the insertion portion 12 such as by being positioned around an outer circumference of the distal end portion 20 of the bending section 26. Thus, the magnetizable element 14 can be any shape, for example a tube or sleeve 28 in construction. The magnetizable element 14 can be positioned at or adjacent the distal tip 21 of the probe 10. The magnetizable element 14 can be made of a known magnetizable material, such as but not limited to a permanent magnet, an electromagnet, a ferrous metal, etc. for example. As illustrated in FIG. 2, the magnetizable element 14 can be arranged transverse (or at another angle) relative to the longitudinal axis LA of the insertion portion 12 at the distal end portion 20 such that a first pole (indicated as a north pole N but can alternatively be a south pole in other examples) of the magnetizable element 14 can be located more closely adjacent to the distal tip 21 of the probe 10 than a second pole (indicated as a south pole S but can alternatively be a north pole in other examples) of the magnetizable element 14. Put another way, a border between the first pole and the second pole can be arranged transverse (or at another angle) relative to the longitudinal axis LA. Thus, the first pole and the second pole can be arranged to extend around or extend across the longitudinal axis LA.

Returning to FIG. 1A, the probe 10 can be part of the aforementioned system 16 that can further include the extracorporeal magnetizable actuator 18A. The extracorporeal magnetizable actuator 18A can be a second magnetizable element 30 (the other being the magnetizable element 14). The second magnetizable element 30 can be made of a magnetizable material, such as but not limited to a permanent magnet, an electromagnet, or a ferrous metal, for example. The extracorporeal magnetizable actuator 18A can be configured to abut or interface with the dermis D of the patient as illustrated. The second magnetizable element 30 can be arranged in a stacked formation such that a first pole (indicated as a south pole S but can alternatively be a north pole in other examples) of the second magnetizable element 30 can be located more closely adjacent to the dermis D of the patient than a second pole (indicated as a north pole N but can alternatively be a south pole in other examples) of the second magnetizable element 30.

The extracorporeal magnetizable actuator 18A in combination with the magnetizable element 14 can be configured for use to provide the magnetic force MF comprising an attraction between the magnetizable element 14 and second magnetizable element 30 (the extracorporeal magnetizable actuator 18A). The magnetic force MF can used to positionally manipulate (e.g., bend, attract, repel, twist, etc.) the distal end portion 20 of the probe 10 within the kidney K to the target location. This magnetic force MF can be between about 0.2 N and about 0.4 N, for example. According to further examples, the magnetic force MF can be between about 0.25 N and about 0.35 N. According to yet further examples, the magnetic force MF can be about 0.3 N.

According to some examples, one of the magnetizable element 14 and second magnetizable element 30 can be an electromagnet. FIG. 1A provides an example where the magnetizable element 14 can comprise the electromagnet. As such, the system 16 and/or the probe 10 can have the second magnetizable actuator 18B configured so current can be selectively provided to the magnetizable element 14 for operation. The second magnetizable actuator 18B can comprise components of separate devices (in some cases part of a device that actuates the needle 15 of FIGS. 4-6) that can be coupled to and utilize and access pathway of the probe 10. Alternatively, the second magnetizable actuator 18B can be part of the probe 10. In some examples, the probe 10 can be configured as a video endoscope (such as a ureteroscope) and can include a control system, and the second magnetizable actuator 18B can be an electromagnetic actuator that can be coupled to the control system of the video endoscope.

Figure 3:
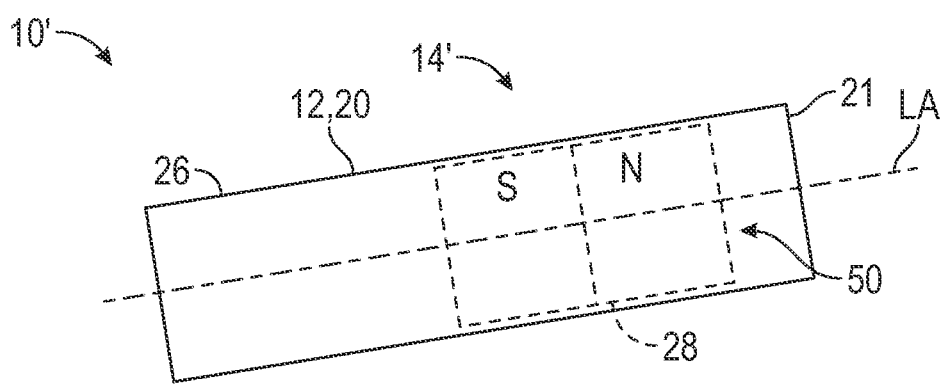
FIG. 3 is an enlarged schematic view of the distal end portion of the probe according to another example of the present application.

FIG. 3 shows an alternative example of a magnetizable element 14' for a probe 10'. The probe 10' and magnetizable element 14' can have a configuration and operation as previously discussed with regard to the probe 10 and the magnetizable element 14. The magnetizable element 14' can differ in that it can be coupled to or can be an integral portion of the insertion portion 12 such as by being inserted in a lumen 50 or recess within an outer circumference of the distal end portion 20 of the bending section 26. Thus, the magnetizable element 14' can again be any shape, for example a tube or sleeve 28 in construction and can be positioned at or adjacent the distal tip 21 of the probe 10. The magnetizable element 14' can be made of the magnetizable material, such as but not limited to a permanent magnet, an electromagnet, or a ferrous metal, for example. As illustrated in FIG. 3, the magnetizable element 14' can be arranged transverse (or at another angle) relative to the longitudinal axis LA of the insertion portion 12 at the distal end portion 20 such that a first pole (indicated as a north pole N but can alternatively be a south pole in other examples) of the magnetizable element 14' can be located more closely adjacent to the distal tip 21 of the probe 10 than a second pole (indicated as a south pole S but can alternatively be a north pole in other examples) of the magnetizable element 14'. Put another way, a border between the first pole and the second pole can be arranged transverse (or at another angle) relative to the longitudinal axis LA. Thus, the first pole and the second pole can be arranged to extend around or extend across the longitudinal axis LA.

Figure 4:
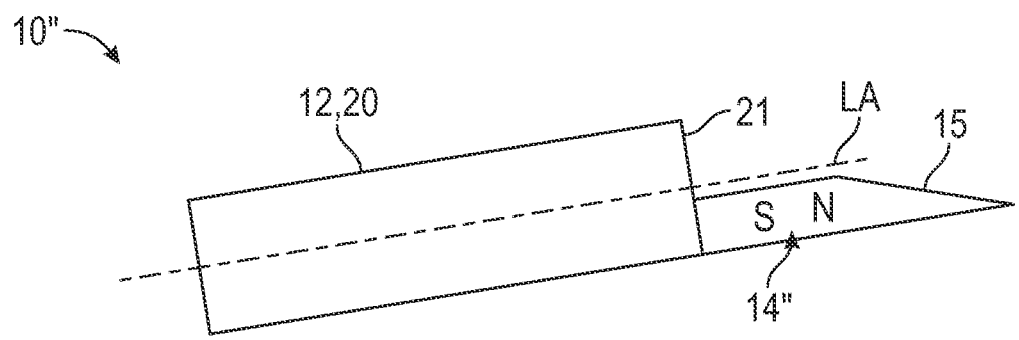
FIG. 4 is an enlarged schematic view of the distal end portion of the probe according to yet another example of the present application.
Figure 5:
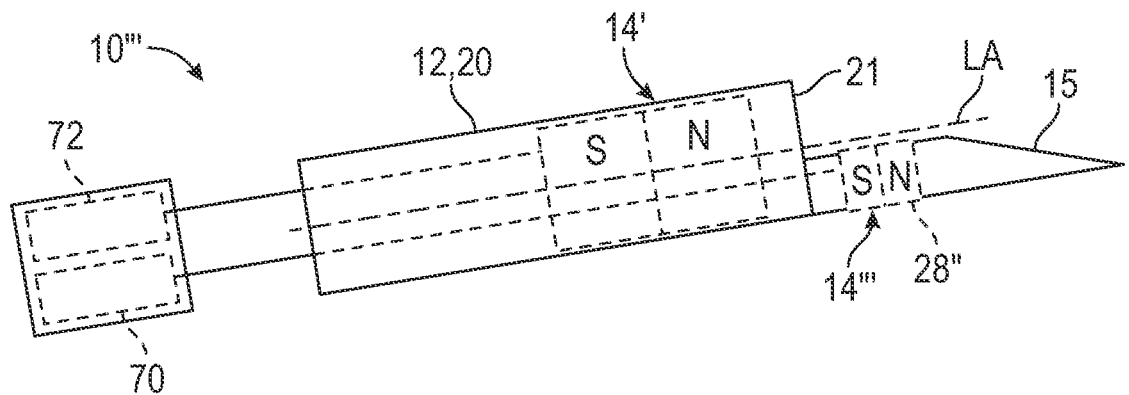
FIG. 5 is an enlarged schematic view of the distal end portion of the probe according to a further example of the present application
Figure 6:
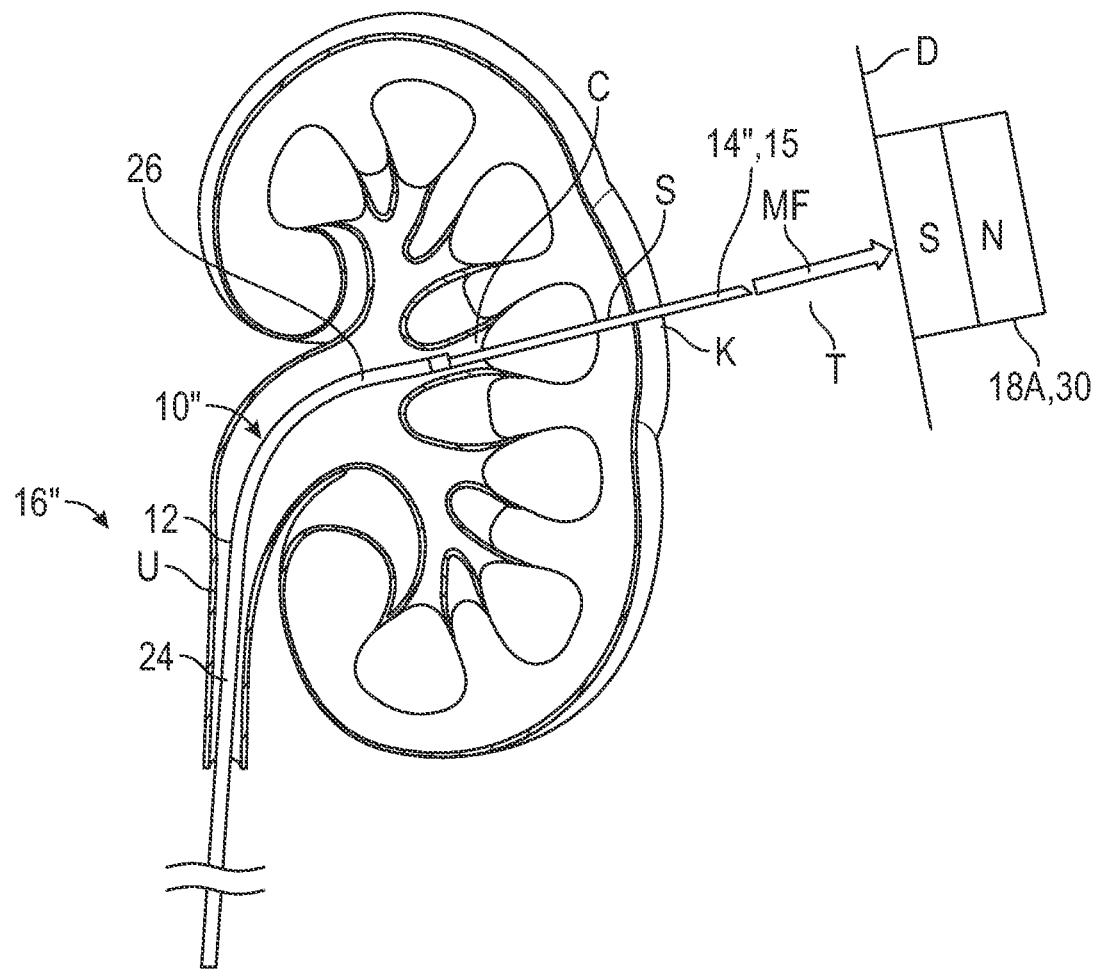
FIG. 6 is a schematic view of the system including the probe and the extracorporeal magnetizable actuator where the magnetic field between the probe and the magnetizable actuator causes the probe to perform a retrograde puncture from the anatomical region of the patient outward toward the magnetizable actuator according to an example the present application.

FIG. 4 shows yet another example of a probe 10". The probe 10" and operation thereof is also illustrated in FIG. 6. As shown in FIG. 4, the probe 10" can have a construction similar to that of the probe 10 or probe 10' previously described. The probe 10" can differ from those of the other probes in that the probe 10" can have a magnetizable element 14" that can comprise or be at least a part of the needle 15 as shown in FIG. 4 or the magnetizable element 14'" can be coupled to the needle 15 as shown in FIG. 5. Put another way, the example of FIG. 4 shows the needle 15 or parts thereof can be constructed of magnetizable material, such as but not limited to a permanent magnet, an electromagnet, or a ferrous metal, for example.

FIG. 5 shows yet another example of a probe 10'". The probe 10'" can have a construction similar to that of the probes previously described. As shown in FIG. 5, the probe 10'" can have a magnetizable element 14'", which can be a sleeve, tube or other separate element 28" that can fit over or be positioned within the needle 15. Additionally, as shown in FIG. 5, the probe 10''' can have a combination of the magnetizable element 14' as previously illustrated and discussed with the magnetizable element 14'''. The magnetizable element 14''' can be an electromagnet, for example and can be selectively actuated on and off to actuate the needle 15. However, both the magnetizable element 14' and the magnetizable element 14''' can be electromagnets according to some examples. As such, the system 16''' (FIG. 6) and/or the probe 10''' can have at least a first magnetizable actuator 70 and/or second magnetizable actuator 72 that can be electronically coupled to the magnetizable element 14' and/or the magnetizable element 14''', respectively. The first magnetizable actuator 70 can be configured so current can be selectively provided to the magnetizable element 14''' for operation to actuate the needle 15 to perform the retrograde puncture. The second magnetizable actuator 72 can also be configured so current can be selectively provided to the magnetizable element 14'. The magnetizable element 14' can be operationally activated to positionally manipulate the distal end portion 20 of the probe 10'''. The magnetizable element 14' can then be deactivated. Then the magnetizable element 14''' can be operationally activated to actuate the needle 15 to perform the retrograde puncture. Thus, the probe 10''' can utilize two magnetizable elements configured for use in vivo. One magnetizable element (here magnetizable element 14') can be selectively used to positionally manipulate the distal end portion of the probe 10'''. The other magnetizable element (magnetizable element 14''') can be selectively used to extend the needle 15 to perform the retrograde puncture.

The needle 15 can be extendable and retractable from the distal tip 21 of the distal end portion 20 of the insertion portion 12. As illustrated in FIGS. 4 and 5, the magnetizable element 14'' and magnetizable element 14''' can be arranged transverse (or at another angle) relative to the longitudinal axis LA of the insertion portion 12 at the distal end portion 20 such that a first pole (indicated as a north pole N but can alternatively be a south pole in other examples) of the magnetizable element 14'', 14''' can be located more closely adjacent to the distal tip of the needle 15 than a second pole (indicated as a south pole S but can alternatively be a north pole in other examples) of the magnetizable element 14'', 14'''. Put another way, a border between the first pole and the second pole can be arranged transverse (or at another angle) relative to the longitudinal axis LA. Thus, the first pole and the second pole can be arranged to extend around or extend across the longitudinal axis LA.

FIG. 6 is a schematic view illustrating a system 16'' similar to that of the system 16 of FIG. 1 but utilizing the probe 10'' of FIG. 4. The system 16'' can include the extracorporeal magnetizable actuator 18A and/or 18B (although extracorporeal magnetizable actuator 18B is not illustrated in the example of FIG. 4) as previously described. As shown in FIG. 4, the probe 10'' can have the needle 15 that can comprise or be coupled with the magnetizable element 14'' as previously described in FIGS. 4 and 5. As such, the needle 15 can be configured to perform the retrograde puncture in response to a magnetic field MF between the magnetizable element 14'' and the extracorporeal magnetizable actuator 18A (configured as a second magnetizable element 30 as previously described in FIG. 1). This retrograde puncture can form an access channel that can extend generally between the target anatomical region (here the calyx C) and the dermis D adjacent to the extracorporeal magnetizable actuator 18A. FIG. 4 shows the probe 10'' in the act of performing the retrograde puncture through tissue T of the patient toward the extracorporeal magnetizable actuator 18A as guided by the attraction between the magnetizable element 14'' and the extracorporeal magnetizable actuator 18A. The magnetic force MF can positionally extend the needle 15 of the probe 10'' to perform the retrograde puncture through the dermis D can be between about 0.9 N and about 1.5 N, for example. According to further examples, the magnetic force MF can be between about 1.1 N and about 1.3 N. According to yet further examples, the magnetic force MF can be about 1.2 N.

Figure 7:
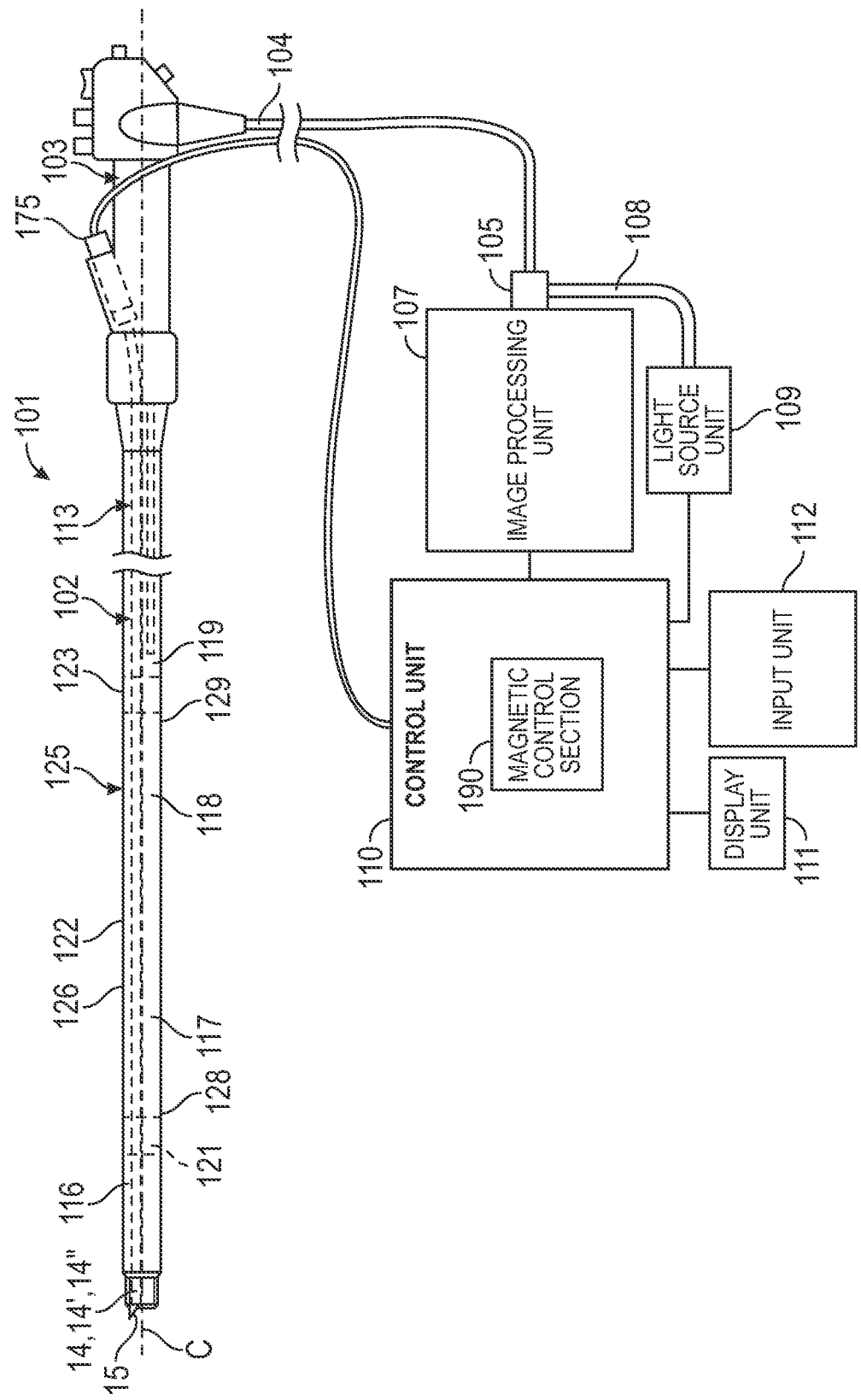
FIG. 7 is a schematic view of an endoscope that can be configured as the probe according to an example of the present application.

FIG. 7 shows an example of an endoscope 101 that can be configured as the probe 10, 10', 10'' or 10''' as previously discussed. Alternatively, the endoscope 101 can be utilized in conjunction with any of the probes and/or needle previously discussed. Thus, for example the endoscope in some examples can be a separate device from the probe and can be configured to provide an access pathway for the insertion portion 12 and the magnetizable element 14', 14'', 14''' (the needle 15 in some examples). FIG. 7 is an example where the endoscope 101 comprises the probe. The endoscope 101 can be used with the system 16 (e.g., extracorporeal magnetizable actuator 18A and/or 18B) as previously described. It should be noted that although the endoscope 101 of FIG. 7 is described as having certain components and features these components and features are optional and need note be present in all examples. The probe as previously discussed and illustrated does not need these components and features as discussed. For example, the magnetic force in some cases can be used to positionally manipulate the distal end portion of the probe (here endoscope 101) within the kidney K to the target location. Furthermore, the endoscope need not have visualization/imaging capability as further described with reference to the example of FIG. 7.

As shown in FIG. 7, the endoscope 101 can include an insertion section 102, and an operation section 103. The operation section 103 can be provided to a proximal direction side of the insertion section 102. The insertion section 102 can be configured to be inserted into a vessel of the patient. One end of a universal cable 104 can be connected to the operation section 103. A scope connector 105 can be provided at the other end of the universal cable 104. The scope connector 105 can be connected to an image processing unit 107 such as an image processor. One end of a light guide tube 108 can be connected to the scope connector 105. The other end of the light guide tube 108 can be connected to a light source unit 109.

The image processing unit 107 and the light source unit 109 can be electrically connected to a control unit 110 such as a personal computer configured to control the entire system of the endoscope 101. Furthermore, a display unit 111 such as a monitor and an input unit 112 such as a keyboard or a mouse can be electrically connected to the control unit 110.

The insertion section 102 can include an elongated insertion main body 113 which can be extended along a longitudinal axis C. The insertion main body 113 can include the emitter 14 provided on a distal end portion, an active bending portion 116 provided to a proximal direction side of the emitter 14, a passive bending portion 117 that can be provided to the proximal direction side of the active bending portion 116 and configured to passively bend upon being subject to an external force, a first flexible portion 118 can be provided to the proximal direction side of the passive bending portion 117, and a second flexible portion 119 can be provided to the proximal direction side of the first flexible portion 118. The active bending portion 116 can be connected to the passive bending portion 117 through a bending tube connecting portion 121. Moreover, the passive bending portion 117 can be connected to the first flexible portion 118 through an intermediate connecting portion 122. Additionally, the first flexible portion 118 can be connected to the second flexible portion 119 through a flexible tube connecting portion 123.

The control unit 110 can include a magnetic control section 190 configured to control operation of the magnetizable element 14, 14' or 14" (e.g., to provide current to the magnetizable element 14, 14', 14" constructed as an electromagnet) to actuate and positionally manipulate the distal end portion of the endoscope 101 within the kidney to the target location or to perform a retrograde puncture as previously illustrated and described, for example. The magnetizable element control section 190 can be operably linked or otherwise related with other operating unit and/or other criteria as desired.

Figure 8:
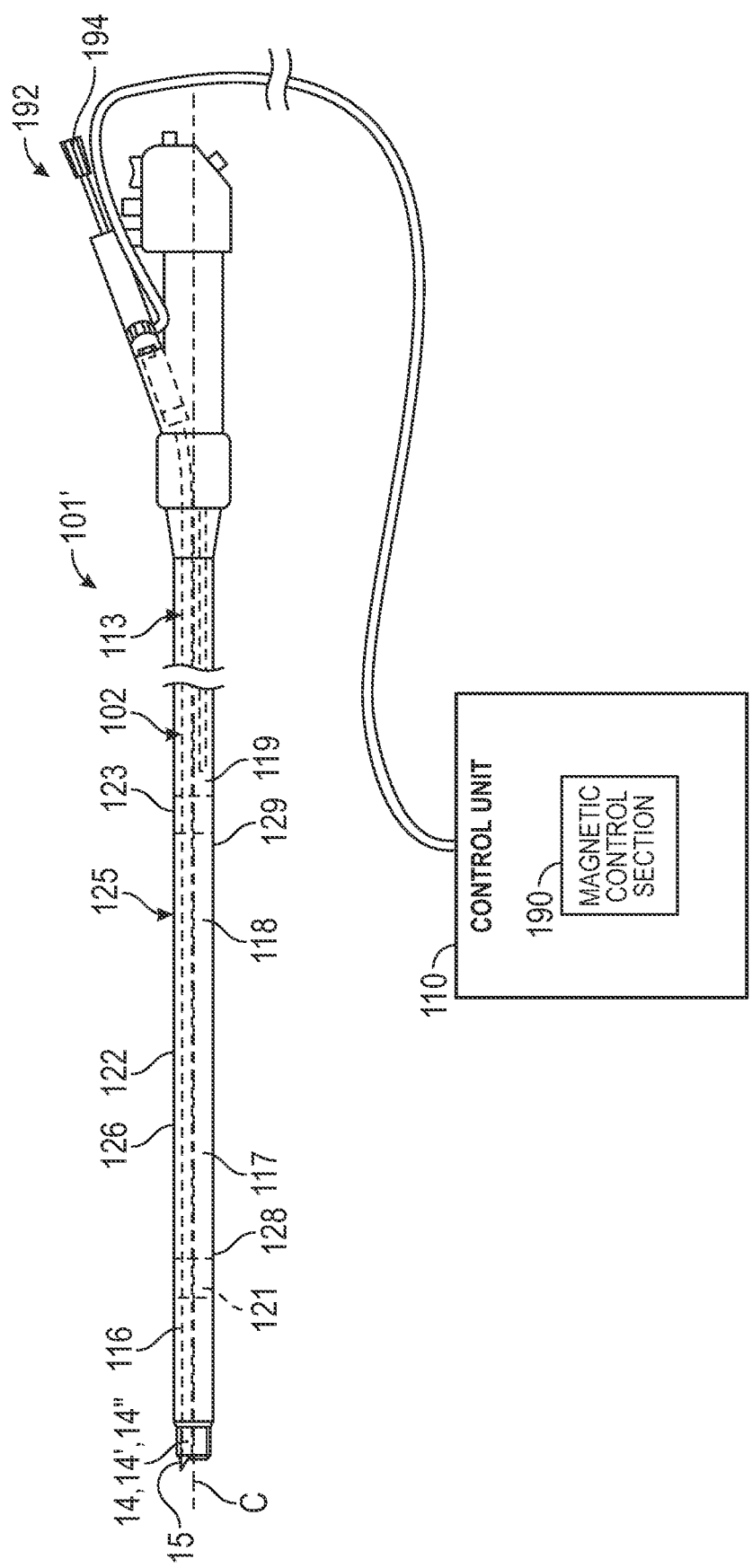
FIG. 8 is a schematic view of the endoscope configured as the probe but with the needle as a separate component that navigates via a working channel of the endoscope according to an example of the present application.

FIG. 8 shows an alternative example of an endoscope 101' that can be configured as the probe 10, 10' or 10" as previously discussed. However, in this example the endoscope 101' can configured to be operable with a separate device 192 having the needle 15 as part thereof. The device 192 can be positioned and can then perform puncture using a working channel of the endoscope 101'. The device 192 can be configured to extend through the endoscope 101' to position the needle 15 at the distal end portion of the endoscope 101' adjacent the magnetizable element 14, 14' or 14". The device 192 can be configured in a manner such as the example of FIG. 5. Thus, the device 192 can have one or more actuators such as actuator 194 to actuate (extend) the needle 15 to perform the retrograde puncture as previously discussed an illustrated. The actuator 194 can be a mechanical actuator or an electromechanical actuator, for example. Thus, the actuator can be a switch, button or other device that can be configured to be selectively actuated to provide current to the magnetizable element coupled to or part of the needle 15 if the magnetizable element is an electromagnet.

Figure 9:
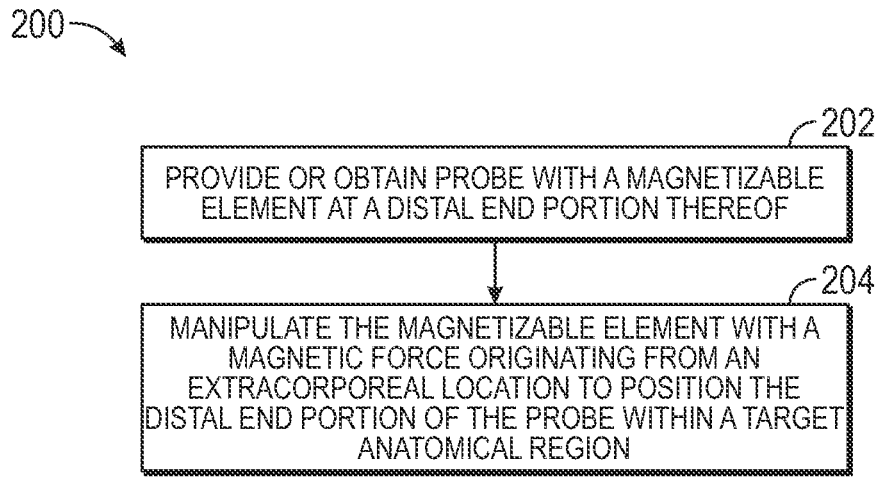
FIG. 9 is a flow diagram of a method for directing a probe to a target anatomical region according to an example of the present application.

FIG. 9 shows a method 200 for directing a probe to a target anatomical region. Although not specifically illustrated in FIG. 8, the method 200 can include an initial insertion of the probe such that the distal end of the probe passes the ureter and is positioned in or adjacent the kidney. Further, positioning of the probe within the kidney according to the method 200 can be performed with endoscopic imaging and with the support of X-ray or another type of imaging (CT, ultrasound, MRI, etc.). Thus, the method 200 can including imaging such as those performed above (or other types) to determine one or more of the target calyx, location of kidney stones, location of the distal end portion, or the like. The imaging discussed herein can be performed contemporaneous with or prior to the positionally manipulating the distal end portion of the probe to the target location or performing the retrograde puncture. It should be noted that after retrograde puncture has been performed a cannula or other access instrument can be inserted in the access. One or more stone fragmentation devices and/or stone retrieval devices can then be utilized with the access pathway created by the needle utilizing the retrograde puncture.

As illustrated in FIG. 9, the method 200 can positionally manipulate the distal end portion of the probe or endoscope within an anatomical structure to a target location (e.g., the calyx). The distal end portion can abutting, aligned with or within close proximity to the calyx of the kidney. The probe can be provided or obtained 202 with a magnetizable element positioned at (e.g., coupled to or as a feature of) the distal end portion of the probe. The magnetizable element can comprise a needle, a sleeve, a tube or another shape as previously described herein. The method 200 can manipulate (e.g., attract) 204 the magnetizable element with a magnetic force originating from an extracorporeal location to position the distal end portion of the probe within the target anatomical region. The manipulating the magnetizable element can comprise bending the distal end portion of the probe to direct a distal tip of the probe toward the target location within the kidney. The magnetic force to position the distal end portion of the probe within the target anatomical region can be between about 0.2 N and about 0.4 N, for example. According to further examples, the magnetic force MF can be between about 0.25 N and about 0.35 N. According to yet further examples, the magnetic force MF can be about 0.3 N.

According to some examples, the positional manipulation can further include performing a retrograde puncture in response to the magnetic field using the needle (which can be or can be coupled to the magnetizable element) to form an access channel that extends generally between the target anatomical region and a dermis or dermal portion adjacent to an extracorporeal magnetizable actuator. The magnetic force to perform the retrograde puncture through or to the dermis D can be between about 0.9 N and about 1.5 N, for example. According to further examples, the magnetic force MF can be between about 1.1 N and about 1.3 N. According to yet further examples, the magnetic force MF can be about 1.2 N.

With either positionally manipulating the distal end portion of the probe to the target location or performing the retrograde puncture, one (or both) of the magnetizable element or the extracorporeal magnetizable actuator can be an electromagnet. Thus, the one of the magnetizable element or the extracorporeal magnetizable actuator can be selectively actuated by providing current thereto to positionally manipulate the distal end of the probe or to trigger the retrograde puncture. If the extracorporeal magnetizable actuator is a permanent magnet, the extracorporeal magnetizable actuator may be placed against or adjacent the dermis only after the the distal end portion of the probe has been passed through the ureter to the kidney. Positioning of the probe within the kidney according to the method 200 can be performed with endoscopic imaging and with the support of X-ray or another type of imaging (CT, ultrasound, MRI, etc.). This imaging can be performed contemporaneous with or prior to the positionally manipulating the distal end portion of the probe to the target location or performing the retrograde puncture.

Figure 10:
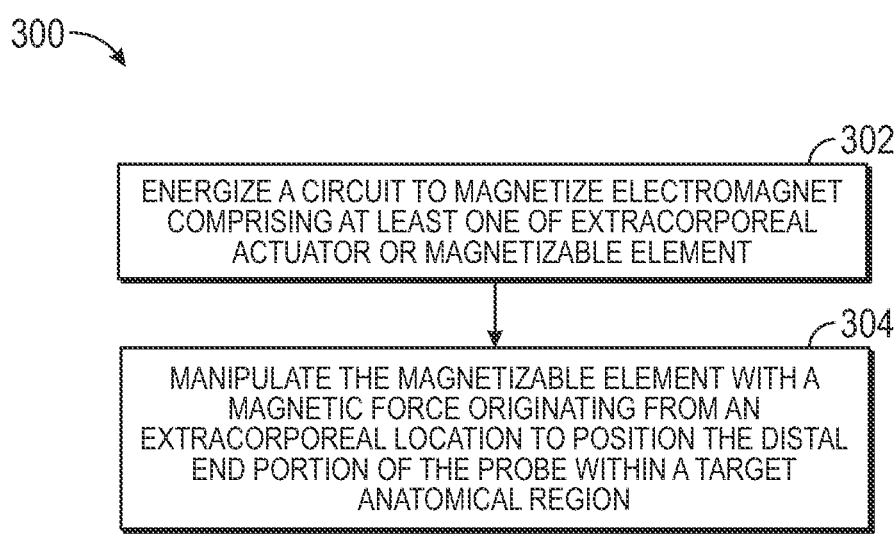
FIG. 10 is a flow diagram of another method of directing the probe to the target anatomical region according to an example of the present application.

FIG. 10 shows a method 300 where at least one of the extracorporeal magnetizable actuator and/or the magnetizable element of the probe (or a device having the needle) can be an electromagnet. Thus, the method 300 can include energizing 302 a circuit to magnetize at least one of the extracorporeal magnetizable actuator and/or the magnetizable element of the probe. The method 300 with the circuit energized can manipulate 304 a distal end portion with the magnetic force between the extracorporeal magnetizable actuator and the magnetizable element of the probe. Such manipulation can include performing retrograde puncture, for example.

According to some examples, the magnetizable element can include two separate magnetizable elements. Both the first magnetizable element and the second magnetizable element can be electromagnets. As such, the method 300 can have two magnetizable actuators, that can be electronically coupled one of the magnetizable elements. The first magnetizable actuator can be configured so current can be selectively provided to the first magnetizable element for operation to actuate the needle to perform the retrograde puncture. The second magnetizable actuator can also be configured so current can be selectively provided to the second magnetizable element. The second magnetizable element can be operationally activated to positionally manipulate the distal end portion of the probe. The second magnetizable element can then be deactivated. Then the first magnetizable element can be operationally activated to actuate the needle to perform the retrograde puncture. Thus, the method 300 can utilize two magnetizable elements configured for use in vivo. One magnetizable element can be selectively used to positionally manipulate the distal end portion of the probe. The other magnetizable element can be selectively used to extend the needle to perform the retrograde puncture.

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A probe for use in an anatomical region of a patient, the probe comprising:
   a proximal portion;
   an insertion portion coupled to the proximal portion and extending distally thereof, the insertion portion having an elongated extent and a longitudinal axis, wherein the insertion portion includes a flexible section;
   a magnetizable element positioned at a distal end portion of the insertion portion and configured for use within the anatomical region to produce a magnetic force of between 0.2 N and 1.5 N between the magnetizable element and an extracorporeal magnetizable element to direct the distal end portion of the probe to a desired location within the anatomic region; and
   a needle extendable from the distal end portion of the probe, wherein the magnetizable element is coupled to or forms at least a part of the needle, and wherein the needle performs a retrograde puncture in response to the magnetic force attracting the magnetizable element toward an extracorporeal magnetizable actuator by translating the needle to advance and thereby form an access channel that extends generally between a target anatomical region and a dermis adjacent to the extracorporeal magnetizable actuator.

2. The probe of claim 1, wherein the needle is a part of a separate device from the probe and passes through a working pathway of the probe to the distal end portion of the probe.

3. The probe of claim 1, wherein the magnetizable element is arranged transverse to a longitudinal axis of the insertion portion at the distal end portion such that a first pole of the magnetizable element is located more closely adjacent to a distal tip of the probe than a second pole of the magnetizable element.

4. The probe of claim 1, wherein the magnetizable element is configured to bend the distal end portion of the probe to the desired location.

5. A puncturing probe for performing a retrograde puncture from a target anatomical region of a patient, the probe comprising:
   an insertion portion configured to access the target anatomical region; and
   a needle coupled to a distal end of the insertion portion, wherein the needle has a magnetizable element that is coupled thereto or that forms at least a part of the needle, and wherein the needle is configured to perform the retrograde puncture in response to a magnetic field having a force of between 0.9 N and 1.5 N of an extracorporeal magnetizable actuator by translating the needle to advance and thereby form an access channel that extends generally between the target anatomical region and a dermis adjacent to the extracorporeal magnetizable actuator.

6. The puncturing probe of claim 5, wherein the magnetizable element comprises a tube or sleeve configured to be inserted in or coupled around the insertion portion or the needle.

7. A system for use in a target anatomical region of a patient, the system comprising:
a probe comprising:
a proximal portion;
an insertion portion coupled to the proximal portion and extending distal thereof, the insertion portion having an elongated extent and a longitudinal axis, wherein the insertion portion includes a flexible section; and
a magnetizable element positioned at a distal end portion of the insertion portion and configured for use within the target anatomical region;
an extracorporeal magnetizable actuator configured to attract the magnetizable element with a magnetic force of between 0.2 N and 1.5 N to direct the distal end portion of the probe to the target anatomical region; and
a needle at the distal end portion of the probe, wherein the magnetizable element is coupled to or forms at least a part of the needle, and wherein the needle performs a retrograde puncture in response to the magnetic force attracting the magnetizable element toward the extracorporeal magnetizable actuator by translating the needle to advance and thereby form an access channel that extends generally between the target anatomical region and a dermis adjacent to the extracorporeal magnetizable actuator.

8. The system of claim 7, wherein the needle is a part of a separate device from the probe and passes through a working pathway of the probe to the distal end portion of the probe.

9. The system of claim 7, wherein the magnetizable element has a first magnet that is configured to be arranged transverse to a longitudinal axis of the insertion portion at the distal end portion such that a first pole of the first magnet is located more closely adjacent to a distal tip of the probe than a second pole of the first magnet, and wherein the extracorporeal magnetizable actuator has a first pole configured to interface with and be more closely adjacent an epidermis than a second pole of the extracorporeal magnetizable actuator.

10. The system of claim 7, wherein one of the extracorporeal magnetizable actuator or the magnetizable element is a user-actuatable electromagnet.

* * * * *